(12) United States Patent
Nunes et al.

(10) Patent No.: US 12,035,932 B1
(45) Date of Patent: Jul. 16, 2024

(54) INTRAVASCULAR LITHOTRIPSY CATHETER WITH SLOTTED EMITTER BANDS

(71) Applicant: Shockwave Medical, Inc., Santa Clara, CA (US)

(72) Inventors: Kevin Nunes, Santa Clara, CA (US); Huy Phan, Santa Clara, CA (US); Hoa Nguyen, Santa Clara, CA (US); Kieran Coghlan, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/137,815

(22) Filed: Apr. 21, 2023

(51) Int. Cl.
*A61B 17/22* (2006.01)
(52) U.S. Cl.
CPC ............ *A61B 17/22022* (2013.01); *A61B 2017/22008* (2013.01); *A61B 2017/22025* (2013.01); *A61B 2017/22094* (2013.01)
(58) Field of Classification Search
CPC ........ A61B 17/22022; A61B 17/22029; A61B 2017/22007; A61B 2017/22021; A61B 2017/22051
See application file for complete search history.

(56) References Cited

U.S. PATENT DOCUMENTS

| | | |
|---|---|---|
| 2,916,647 A | 12/1959 | George |
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

International Search Report and Written Opinion received for International Application No. PCT/US2023/086441 mailed May 3, 2024, 9 pages.

*Primary Examiner* — Sarah W Aleman
(74) *Attorney, Agent, or Firm* — Morrison & Foerster LLP

(57) ABSTRACT

A catheter for treating an occlusion in a body lumen includes an elongate tube; a member sealed to a distal end of the elongate tube that is fillable with a conductive fluid; a cylindrical conductive sheath circumferentially mounted around the elongate tube within the member, the conductive sheath comprising a slot extending along a length of the conductive sheath; and a wire at least partially disposed in the slot, wherein a distal end of the wire is spaced apart from the conductive sheath by a gap in an arrangement such that when a voltage pulse is supplied to the insulated wire current flows across the gap to generate cavitation bubbles and/or shock waves.

21 Claims, 9 Drawing Sheets

(56) References Cited

U.S. PATENT DOCUMENTS

| | | |
|---|---|---|
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzel |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,505,702 A | 4/1996 | Arney |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,697,281 A | 12/1997 | Eggers et al. |
| 5,709,676 A | 1/1998 | Alt |
| 5,735,811 A | 4/1998 | Brisken |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,404 B1 | 4/2001 | Shadduck |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,061 B1 | 8/2002 | Wenner et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 * | 6/2004 | Fry ............ A61N 7/00 606/7 |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,267,654 B2 * | 9/2007 | Matula ............ A61B 17/22004 601/3 |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,618,432 B2 | 11/2009 | Pedersen et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 * | 6/2015 | Hawkins ............ A61M 25/1002 |
| 9,072,534 B2 | 7/2015 | Adams et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,517,620 B2 | 12/2019 | Adams |
| 10,517,621 B1 | 12/2019 | Adams |
| 10,555,744 B2 * | 2/2020 | Nguyen ............ A61B 17/22004 |
| 10,682,178 B2 | 6/2020 | Adams et al. |
| 10,702,293 B2 | 7/2020 | Adams et al. |
| 10,709,462 B2 * | 7/2020 | Nguyen ............ A61B 17/2202 |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Hakala et al. |
| 11,534,187 B2 | 12/2022 | Bonutti |
| 11,596,424 B2 | 3/2023 | Hakala et al. |

(56) References Cited

U.S. PATENT DOCUMENTS

| | | |
|---|---|---|
| 11,622,780 B2 | 4/2023 | Nguyen et al. |
| 11,696,799 B2 | 7/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0163081 A1 | 8/2003 | Constantz et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0082859 A1 | 4/2004 | Schaer |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090846 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069385 A1 | 3/2006 | Lafontaine et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0077165 A1 | 3/2008 | Murphy |
| 2008/0097251 A1 | 4/2008 | Babaev |
| 2008/0188913 A1 | 8/2008 | Stone et al. |
| 2009/0030503 A1 | 1/2009 | Ho |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2010/0324554 A1 | 12/2010 | Gifford et al. |
| 2011/0034832 A1* | 2/2011 | Cioanta ............ A61B 17/22012 601/1 |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall |
| 2012/0157991 A1 | 6/2012 | Christian |
| 2012/0203255 A1 | 8/2012 | Hawkins et al. |
| 2012/0221013 A1 | 8/2012 | Hawkins et al. |
| 2012/0253358 A1 | 10/2012 | Golan |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0039514 A1 | 2/2014 | Adams et al. |
| 2014/0046229 A1 | 2/2014 | Hawkins et al. |
| 2014/0046353 A1 | 2/2014 | Adams |
| 2014/0163592 A1 | 6/2014 | Hawkins et al. |
| 2014/0214061 A1 | 7/2014 | Adams et al. |
| 2015/0238209 A1 | 8/2015 | Hawkins et al. |
| 2015/0320432 A1 | 11/2015 | Adams |
| 2016/0135828 A1 | 5/2016 | Hawkins et al. |
| 2016/0151081 A1 | 6/2016 | Adams et al. |
| 2016/0184570 A1 | 6/2016 | Grace et al. |
| 2016/0324534 A1 | 11/2016 | Hawkins et al. |
| 2017/0135709 A1 | 5/2017 | Nguyen et al. |
| 2019/0388110 A1 | 12/2019 | Nguyen et al. |
| 2020/0085458 A1 | 3/2020 | Nguyen et al. |
| 2021/0085347 A1* | 3/2021 | Phan ................ A61B 17/22012 |
| 2021/0085383 A1 | 3/2021 | Vo et al. |
| 2021/0282792 A1 | 9/2021 | Adams et al. |
| 2021/0338258 A1 | 11/2021 | Hawkins et al. |
| 2022/0015785 A1 | 1/2022 | Hakala et al. |
| 2022/0183708 A1 | 6/2022 | Phan et al. |
| 2022/0240958 A1 | 8/2022 | Nguyen et al. |
| 2023/0043475 A1 | 2/2023 | Adams |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| DE | 3038445 A1 | 5/1982 |
| DE | 202006014285 U1 | 12/2006 |
| EP | 442199 A2 | 8/1991 |
| EP | 571306 A1 | 11/1993 |
| EP | 623360 A1 | 11/1994 |
| EP | 647435 A1 | 4/1995 |
| EP | 2253884 A1 | 11/2010 |
| EP | 2362798 B1 | 4/2014 |
| EP | 3434209 A | 1/2019 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-047135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2008506447 A | 12/2004 |
| JP | 2011513694 A | 12/2004 |
| JP | 2011520248 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |

(56) References Cited

FOREIGN PATENT DOCUMENTS

| | | |
|---|---|---|
| JP | 2011524203 A | 9/2011 |
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2021061451 A1 | 4/2021 |

\* cited by examiner

← Backward　　　　　　　　　　　　Forward →

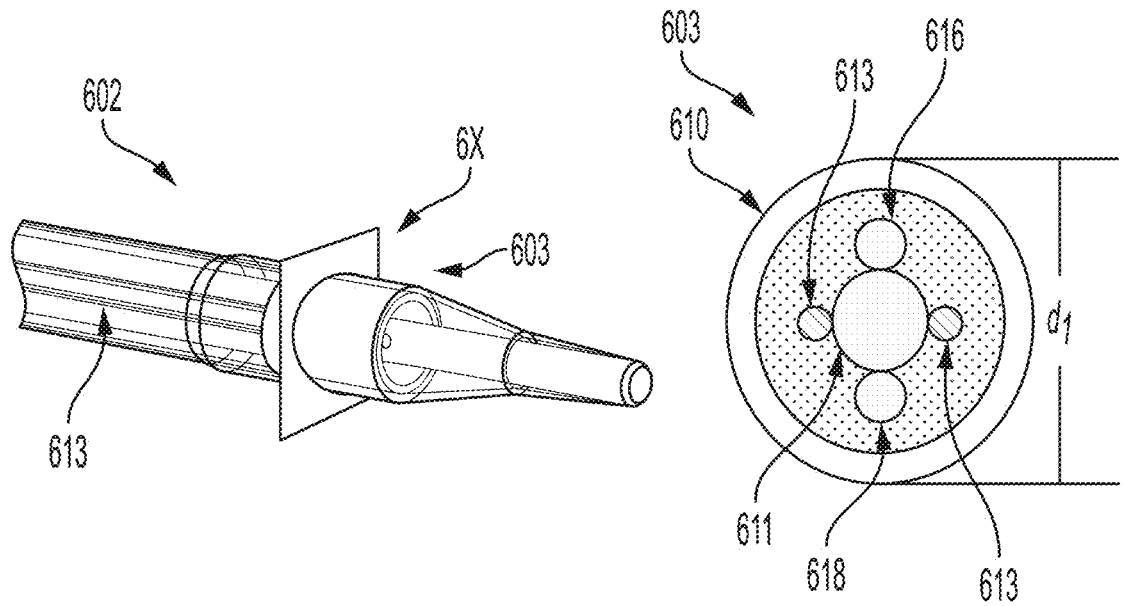
FIG. 6A
FIG. 6B
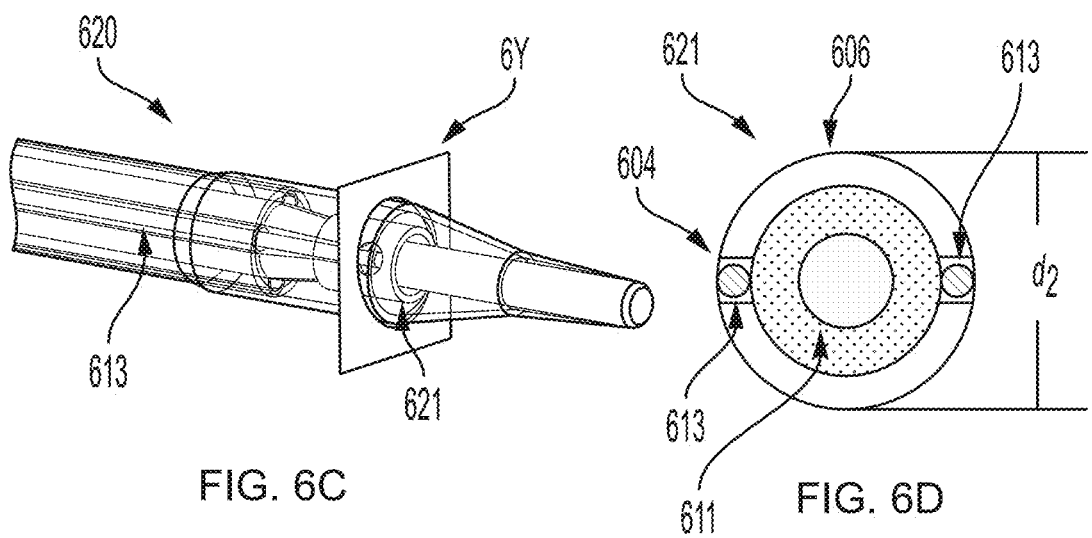
FIG. 6C
FIG. 6D

INTRAVASCULAR LITHOTRIPSY CATHETER WITH SLOTTED EMITTER BANDS

FIELD OF THE DISCLOSURE

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel or non-calcified plaque.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion, but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

Efforts have been made to improve the delivery of shock waves in these devices. For instance, forward-biased designs, such as the designs found in U.S. Pat. No. 10,966,737 and U.S. Publication No. 2019/0388110, both of which are incorporated herein by reference, direct shock waves in a generally forward direction (e.g., distally from the distal end of a catheter) to break up tighter and harder-to-cross occlusions in vasculature. Other catheter devices have been designed to include arrays of low-profile electrode assemblies that reduce the crossing profile of the catheter and allow the catheter to more easily navigate calcified vessels to deliver shock waves in more severely occluded regions of vasculature. For instance, U.S. Pat. Nos. 8,888,788, and 10,709,462 and U.S. Publication No. 2021/0085347, each of which is incorporated herein by reference, provide examples of low-profile electrode assemblies. Such forward-biased and low-profile designs are particularly useful when an artery is totally or partially occluded, for example, with thrombus, plaque, fibrous plaque, and/or calcium deposits. When treating such conditions, a physician must first cross the occlusion (e.g., pass through the occluded area), and then feed the angioplasty balloon and/or other tools down the artery to the blockage to perform the desired procedure. In some instances, however, such as the case of a chronic total occlusion ("CTO"), the occlusion may be so tight and solid that it is difficult to cross the treatment device into the true lumen of the distal vessel. Some physicians may implement atherectomy procedures (e.g., laser-based, mechanically cutting or shaving, mechanically rotating devices, etc.) to form a channel in a CTO in combination with an angioplasty balloon treatment, but many atherectomy devices and systems carry a higher risk of vessel perforation or vessel dissection as compared with a basic angioplasty balloon catheters.

Despite these advances, currently available shock wave catheters can encounter challenges treating CTOs. First, the navigability of the catheter in a CTO is limited by the crossing profile of the device. While certain low-profile designs improve the overall navigability of the device, even further crossing profile reductions can be necessary to navigate severely occluded vessels. Second, when navigating severely occluded vessels, the direction that the shock waves travel can dictate the ability to advance the catheter farther. Thus, it may be desirable to implement a forward-biased design in order to soften, weaken, or break up occlusions in vasculature such that the catheter can be incrementally advanced farther within the occlusion. Accordingly, there is an unmet need for low-profile catheter designs capable of producing forward-biased acoustic shock waves. Similar devices are needed for treating occlusions formed in other parts of the body, for example, kidney stones in the urinary system.

SUMMARY

The above objectives are realized in a catheter that includes an electrode assembly with a cylindrical conductive sheath comprising one or more slots that provide a recessed location for the placement of insulated wires. The insulated wires can include a non-insulated distal end that forms a first electrode, while the conductive sheath forms the second electrode of an electrode pair. When voltage is supplied to the insulated wires, shock waves are emitted from the electrode pair. Placing the wire in the slot enables placing the non-insulated distal end of the wire closely proximate to the distal end of the conductive sheath which promotes forward-biasing of the shock waves emitted from the electrode pair. Moreover, placing the wire in the slot also reduces the crossing profile of the emitter in comparison to a design wherein the wire is located on an inside surface of the conductive sheath. Thus, the slotted emitter configuration enables the catheter to navigate more severely occluded vessels by focusing the shock waves in a forward direction to break up occlusion forward of the device and reducing the profile of the device such that the catheter can navigate smaller channels.

The disclosure provides a catheter for treating occlusions in a body lumen, such as within blood vessels. The catheter can include an elongate tube with a member sealed to a distal end of the elongate tube that is fillable with a conductive fluid. The member can surround a cylindrical conductive sheath (e.g., an "emitter sheath") that is circumferentially mounted around the elongate tube. The conductive sheath has at least one slot extending along a length of the conductive sheath. An insulated wire having a non-insulated distal end is positioned in the slot such that both an insulated portion and the non-insulated portion of the wire is disposed in the slot. The non-insulated distal end of the wire is spaced apart from the conductive sheath by a gap. When a voltage pulse is supplied to the insulated wire, such as via a pulsed voltage source, current flows across the gap to generate cavitation bubbles and/or shock waves. The cavitation bubbles and/or shock waves break apart occlusions in the body lumen.

The slots of the conductive sheath enable placement of the non-insulated portion of the insulated wire proximate to the distal end of the conductive sheath, which promotes forward-biased cavitation bubbles and/or shock waves. Forward biased or distally directed (these terms are used interchangeably herein) cavitation bubbles and/or shock waves enables the catheter of the invention to be advanced farther within tight occlusions (or CTOs after creating a channel). The slots of the conductive sheath also provide a recessed location for the placement of the insulated wires, which reduces the overall diameter of the distal end of the catheter relative to a catheter that includes a cylindrical sheath that surrounds insulated wires. The elongate tube can also include grooves for placement of the insulated wires that provide a recessed location for the length of the wire that extends from a proximal side of the catheter (e.g., outside a patient) to the emitter near a distal end of the catheter (e.g., proximate to a treatment location). Placing the wires in grooves of the elongate tube similarly reduces the overall diameter of the catheter relative to a design that does not include grooves, which further improves the ability of the catheter according to the invention to treat tight occlusions and/or CTOs.

According to an aspect, a catheter for treating an occlusion in a body lumen includes an elongate tube; a member sealed to a distal end of the elongate tube that is fillable with a conductive fluid; a cylindrical conductive sheath circumferentially mounted around the elongate tube within the member, the conductive sheath comprising a slot extending along a length of the conductive sheath; and a wire at least partially disposed in the slot, wherein a distal end of the wire is spaced apart from the conductive sheath by a gap in an arrangement such that when a voltage pulse is supplied to the insulated wire current flows across the gap to generate cavitation bubbles and/or shock waves.

A majority of the at least a portion of the wire that is in the slot may be insulated. The catheter may include a second wire that is connected to the conductive sheath. The second wire may be connected to a proximal end of the conductive sheath.

The slot may terminate with a cutout, and the non-insulated distal end of the insulated wire may be positioned in the cutout. The cutout may be spaced apart from a distal end of the conductive sheath. The cutout may have a circular shape.

The conductive sheath may include a longitudinal axis and at least a portion of the slot may extend circumferentially around the conductive sheath with respect to the longitudinal axis. The slot may include a helical shape. The slot may extend along the entire length of the conductive sheath.

The slot may be a first slot and the insulated wire may be a first insulated wire, and the catheter may include a second slot extending along the length of the conductive sheath; and a second insulated wire having an insulated portion and a non-insulated distal end, where the insulated portion and the non-insulated distal end are disposed in the second slot; wherein the non-insulated distal end is spaced apart from the conductive sheath by a gap in an arrangement such that when the voltage pulse is supplied to the first insulated wire and the second insulated wire, current flows across the gap between the non-insulated distal end of the first insulated wire and the conductive sheath and across the gap between the non-insulated distal end of the second insulated wire and the conductive sheath to generate cavitation bubbles and/or shock waves at each gap.

The elongate tube may include at least one groove extending along a length of the elongate tube, and wherein the insulated wire extends along the at least one groove of the elongate tube. The insulated wire may include an insulating layer wrapping around a length of the insulated wire, wherein the distal end of the insulated wire is exposed from the insulating layer to form the non-insulated distal end.

The insulated wire may include an insulating layer wrapping around the insulated wire, and wherein a strip of the insulating layer is removed to form the non-insulated distal end. The at least a portion of the insulated wire may be flattened. The elongate tube may include a guidewire lumen for receiving a guidewire, wherein the catheter is configured to be advanced into the body lumen over the guidewire. The elongate tube may include one or more flush lumens for removing the cavitation bubbles and/or shock waves from within the member.

According to an aspect, a system for treating an occlusion in a body lumen includes a catheter that includes an elongate tube; a member sealed to a distal end of the elongate tube that is fillable with a conductive fluid; a cylindrical conductive sheath circumferentially mounted around the elongate tube within the member, the conductive sheath comprising a first slot and a second slot extending along a length of the conductive sheath; a first insulated wire having an insulated portion and a non-insulated distal end, both the insulated portion and the non-insulated distal end being disposed in the first slot wherein the non-insulated distal end is and spaced apart from the conductive sheath by a gap; a second insulated wire having an insulated portion and a non-insulated distal end, both the insulated portion and the non-insulated distal end being disposed in the second slot, wherein the non-insulated distal end is and spaced apart from the conductive sheath by a gap; and a power source that supplies the first insulated wire and the second insulated wire with a voltage pulse causing current to flow across the gap between the non-insulated distal end of the first insulated wire and the conductive sheath and the gap between the non-insulated distal end of the second insulated wire and the conductive sheath to generate cavitation bubbles and/or shock waves at each gap.

A majority of a length of the first slot may include the insulated portion of the first insulated wire and a majority of a length of the second slot may include the insulated portion of the second insulated wire. The first slot may terminate with a cutout that is spaced apart from a distal end of the conductive sheath, and the non-insulated distal end of the first insulated wire may be positioned in the cutout and the second slot extends along the entire length of the conductive sheath.

The first slot and the second slot each may terminate with a cutout that is spaced apart from a distal end of the conductive sheath, wherein the non-insulated distal end of the first insulated wire is positioned in the cutout of the first slot and the non-insulated distal end of the second insulated wire is positioned in the cutout of the second slot. The cutout of each of first slot and the second slot may have a circular shape.

The conductive sheath may include a longitudinal axis and at least a portion of the slot may extend circumferentially around the conductive sheath with respect to the longitudinal axis. The slot may have a helical shape.

DESCRIPTION OF THE FIGURES

Illustrative aspects of the present disclosure are described in detail below with reference to the following figures. It is intended that the embodiments and figures disclosed herein are to be considered illustrative and exemplary rather than restrictive.

FIG. 6A illustrates the distal end of an exemplary catheter with a conventional shock wave generator, according to aspects of the present disclosure;

FIG. 6B illustrates a cross sectional view of the catheter of FIG. 6A, according to aspects of the present disclosure;

FIG. 6C illustrates the distal end of an exemplary catheter with a shock wave generator having a slotted emitter, according to aspects of the present disclosure; and FIG. 6D illustrates a cross sectional view of the catheter of FIG. 6C, according to aspects of the present disclosure.

DETAILED DESCRIPTION

Figure 1:
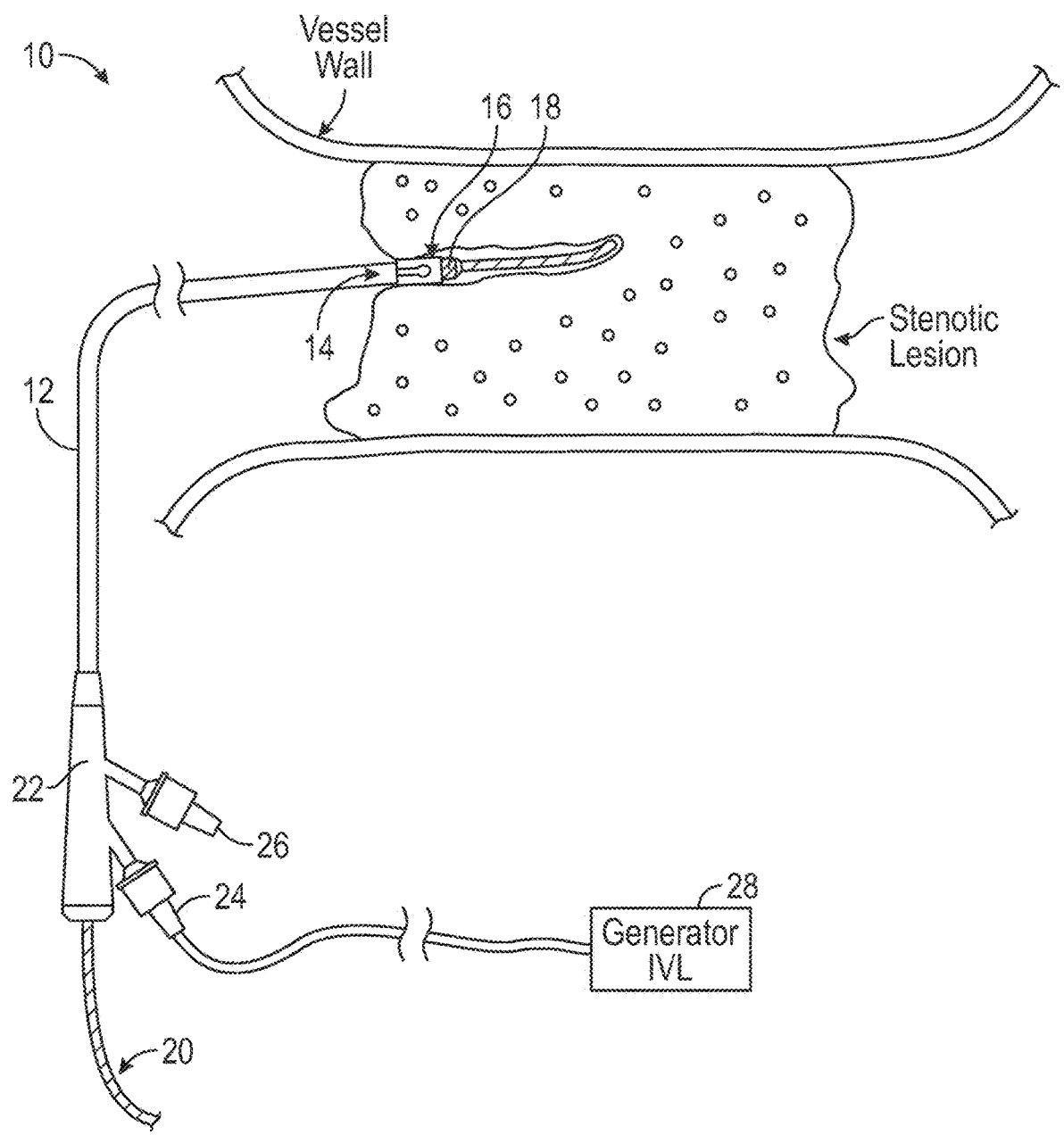
FIG. 1 illustrates an exemplary shock wave angioplasty catheter being used to treat an occlusion in a blood vessel, according to one or more aspects of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The term "emitter sheath" refers to a sheath of conductive material that may form one or more electrodes of one or more electrode pairs, thereby forming a location of one or more emitters.

Described herein are catheters incorporating design elements that reduce the overall diameter of the catheter and promote forward-biased shock waves, which enables the catheter to treat tighter, hard-to-cross calcified lesions and chronic total occlusions. The present invention is similar to existing IVL systems in that it can comprise an array of lithotripsy emitters (e.g., electrode pairs) on a catheter that is inserted into a patient's vasculature to deliver shock waves to an occlusion. However, the present invention incorporates emitter sheaths with slots that provide a recessed location such that the insulated wires that deliver voltage to the emitter can be positioned within the slots and reduce the overall diameter of the catheter. Furthermore, placing the insulated wires within the slots also enables forward-biased shock waves by placing a non-insulated portion of the wires proximate to a distal end of the emitter, thereby improving the catheter's ability to break up occlusions located forward of or distal to the device (e.g., in front of the device). The forward-biased design and reduced profile catheter can thus generate channels through occluded vessels and navigate smaller channels in occluded vessels, thereby enabling the catheter to treat hard-to-cross calcified lesions. It should be appreciated that forward-biased shock waves are directed toward and/or past the distal end of the catheter devices described herein.

FIG. 1 illustrates an exemplary shock wave angioplasty catheter 10 being used to treat an occlusion in a blood vessel, according to one or more aspects of the present disclosure. The catheter 10 is advanced into an occlusion in a patient's vasculature, such as the stenotic lesion depicted in FIG. 1, over a guidewire 20 carried in a guidewire sheath. A distal end 14 of the catheter 10 includes a shock wave generator 16 that produces shock waves at one or more emitters (e.g., electrode pairs) to break up calcified lesions. As used herein, each of the one or more emitters include electrode pairs having first and second electrodes separated by a gap, at which shock waves are formed when a current flows across the gap between the electrodes of the pair (i.e., when a voltage is applied across the first and second electrodes). The electrode pairs are arranged in a low-profile configuration that reduces the diameter of the distal end 14 of the catheter 10 and permits the treatment of tight, hard-to-cross lesions. In one or more examples, the shock wave generator 16 includes one or more coplanar electrode pairs or includes one or more electrodes at least partially recessed into the catheter 10.

A flexible cap 18 (e.g., a low-profile flexible angioplasty balloon, a polymer membrane in tension that can flex outward, etc.) is sealably attached to the distal end 14 of the catheter 10, forming an annular channel around the shaft 12 of the catheter. The flexible cap 18 surrounds the shock wave generator 16, such that the shock waves are produced in a closed system within the flexible cap 18. The flexible cap 18 is filled with a conductive fluid, such as saline. The flexible cap 18 can alternatively be referred to as a "window", in particular for implementations where when the interior volume is filled with a fluid and pressurized, the window maintains a substantively constant volume and profile. The conductive fluid allows the acoustic shock waves to propagate outwardly from the electrode pairs of the shock wave generator 16 through the walls of the flexible cap 18 and then into the target lesion. In one or more examples, the conductive fluid may also contain x-ray contrast fluid to permit fluoroscopic viewing of the catheter 10 during use. In some implementations, the material that forms the primary surface(s) of the flexible cap 18 through which shock waves pass can be a non-compliant polymer. In other implementations, a rigid and inflexible structure may be used in lieu of flexible cap 18.

The catheter 10 includes a proximal end 22 (or handle) that remains outside of a patient's vasculature during treatment. The proximal end 22 includes an entry port for receiving the guidewire 20. The proximal end 22 also includes a fluid port 26 for receiving a conductive fluid for filling and emptying the flexible cap during treatment. An electrical connection port 24 is also located on the proximal end 22 to provide an electrical connection between the distal shock wave generator 16 and an external pulsed high voltage source 28, such as the intravascular lithotripsy (IVL) generator shown in FIG. 1.

The catheter 10 also includes a flexible shaft 12 that extends from the proximal end 22 to the distal end 14 of the catheter. The shaft 12 provides various internal conduits connecting elements of the distal end 14 with the proximal end 22 of the catheter (see, e.g., FIG. 6D for a cross-section of a region an exemplary shaft). The shaft 12 includes an elongate tube that includes a lumen for receiving the guidewire 20. The elongate tube may include additional lumens extending through the shaft 12 or along an outer surface of the shaft 12. For example, one for fluid lumens (e.g., a fluid inlet lumen and a fluid outlet lumen or a combined flush lumen) can be located along or within the shaft 12 for carrying conductive fluid from the fluid port 26 into the flexible cap 18.

Figure 2A:
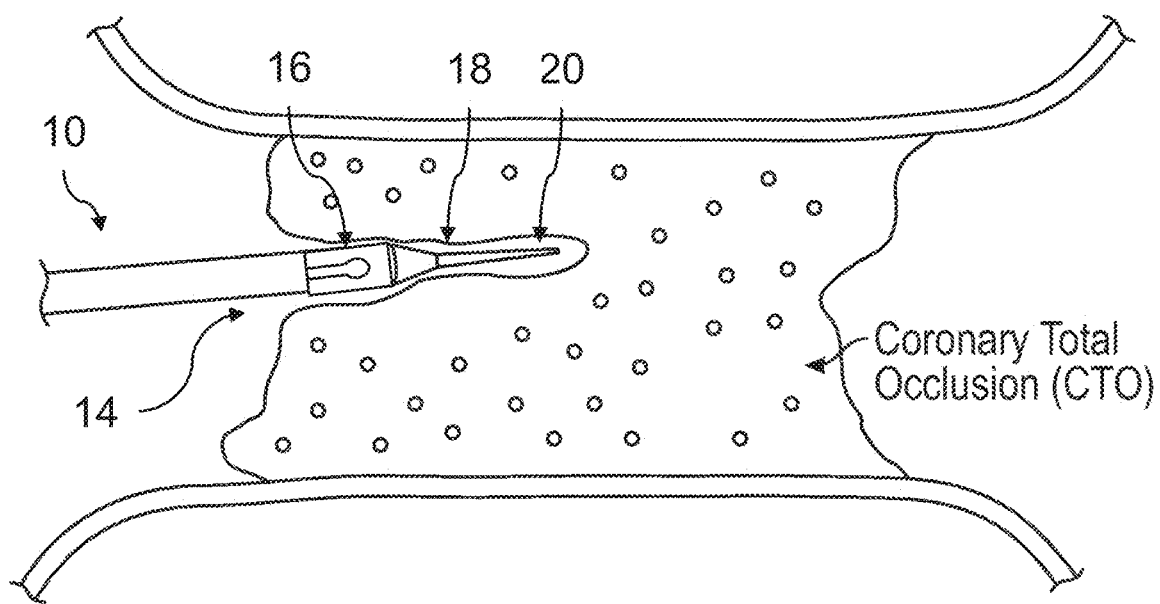
FIG. 2A illustrates an exemplary shock wave angioplasty catheter being used to treat a chronic total occlusion (CTO), according to one or more aspects of the present disclosure.

FIG. 2A illustrates the catheter 10 being used to treat a total occlusion in a blood vessel, for instance, a coronary chronic total occlusion (CTO). In operation, a physician advances the guidewire 20 from an entry site on a patient (e.g., an artery in the groin area of the leg) to the target region of a vessel (e.g., a region having an occlusion that needs to be broken up). The catheter 10 is then advanced over the guidewire 20 to the target region of the vessel. In one or more examples, the flexible cap 18 sealed to the distal end 14 is a no-fold balloon having a low profile when deflated, such that the balloon does not need to be folded while the device is advanced through the vasculature. In other examples, the flexible cap 18 may be membrane that is held in tension by a frame that can flex outwardly when pressurized with conductive fluid. During the positioning stage of treatment, a guide catheter or outer jacket may be used to aid the entry and maneuvering of the catheter 10 within the vasculature. The outer jacket can provide tubular linear support to the catheter shaft 12 and retain the shape of the flexible cap 18 during pushing, crossing, and placement of the catheter 10. The in-situ location of the distal end 14 of the catheter 10 may be determined by x-ray imagining and/or fluoroscopy.

When treating a total occlusion as shown in FIG. 2A, the guidewire 20 is advanced at least partially into the stenotic lesion. The flexible cap 18 is then pressurized with a conductive fluid (e.g., saline and/or saline mixed with an image contrast agent) that is introduced via the fluid port 26, allowing the conductive fluid to expand the flexible cap 18 so that the outer surface of the flexible cap 18 contacts the target lesion. The flexible cap 18 can be pressurized to IVL pressure, which can be between approximately one atmosphere and approximately six atmospheres. When depressurized, the diameter of the distal end 14 of the catheter 10 may be less than 1.5 mm. For instance, the overall diameter of the distal end 14 may be 1.0 mm 1.2 mm, 1.3, mm, or 1.4 mm, and increments and gradients of range therein. In one or more examples, the overall diameter of the distal end 14 may be less than 1.0 mm. The diameter of the flexible cap in a pressurized state may be no more than about 10-15% greater than the diameter of the flexible cap in a depressurized state. However, in some examples, the diameter of the flexible cap 18 in the pressurized state is less than 10% greater than the diameter of the flexible cap 18 in the depressurized state. The flexible cap 18 may be configured such that when it is pressurized (e.g., as a "window"), the profile of the flexible cap 18 remains the same, or nearly the same, as the profile of the flexible cap 18 in the depressurized state. That is, the overall diameter of the flexible cap 18 can be the same, or nearly the same, in the pressurized and depressurized states (e.g., the diameter of the device when pressurized and depressurized is within 5-10% of each other). In all such implementations, the catheter 10 and its flexible cap 18 maintains a consistent low profile throughout therapy.

After inflating the flexible cap 18, a voltage pulse is applied by the voltage source 28 across the one or more electrode pairs (i.e., emitters of the shock wave generator 16). Each pulse initially ionizes the conductive fluid inside the flexible cap 18 to create small gas bubbles around the shock wave generator 16 that insulate the electrodes. Fluid can be continuously flowed into the flexible cap 18 and evacuated via a flush lumen at a constant rate to clear bubbles and debris from the electrodes. The fluid flow rate may be controlled throughout treatment, but is generally in the range of approximately one to three milliliters per minute (1-3 ml/min). Subsequently, a plasma arc forms across a gap between the electrodes of the electrode pairs, creating a low impedance path where current flows freely. The heat from the plasma arc heats the conductive fluid to create a rapidly expanding vapor bubble. The expansion and collapse of the vapor bubble creates a shock wave that propagates through the fluid in the flexible cap 18, through the walls of the flexible cap 18, and into the nearby occlusion where the energy breaks up the hardened lesion.

For treatment of an occlusion in a blood vessel, the voltage pulse applied by the voltage source 28 is typically in the range of from about two thousand to three thousand volts (2,000-3,000 V). In some implementations, the voltage pulse applied by the voltage source can be up to about ten thousand volts (10,000 V). The pulse width of the applied voltage pulses ranges between two microseconds and six microseconds (2-6 µs). The repetition rate or frequency of the applied voltage pulses may be between about 1 Hz and 10 Hz. The total number of pulses applied by the voltage source 28 may be, for example, sixty (60) pulses, eighty (80) pulses, one hundred twenty (120) pulses, three hundred (300) pulses, or up to five hundred (500) pulses, or other increments of pulses within this range. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage form the voltage source 28. More information about the physics of shock wave generation and their control can be found in U.S. Pat. Nos. 8,956,371; 8,728,091; 9,522,012; and 10,226,265, each of which is incorporated by reference.

The progress of the procedure may be monitored by x-ray and/or fluoroscopy. As the lesion is broken up or loosened by the shock waves, the guidewire and catheter can be advanced farther into the lesion, and the shock wave treatment can be repeated until the total occlusion is cleared or until the diameter of the vessel permits the placement of a second treatment device having a larger profile. For example, the enlarged channel can receive a different catheter having a more conventional angioplasty balloon or differently oriented shock wave sources. Catheters of this type are described in U.S. Pat. No. 8,747,416 and U.S. Publication No. 2019/0150960, cited above. Once the lesion has been sufficiently treated, the catheter 10 and the guidewire 20 can be withdrawn from the patient.

Figure 2B:
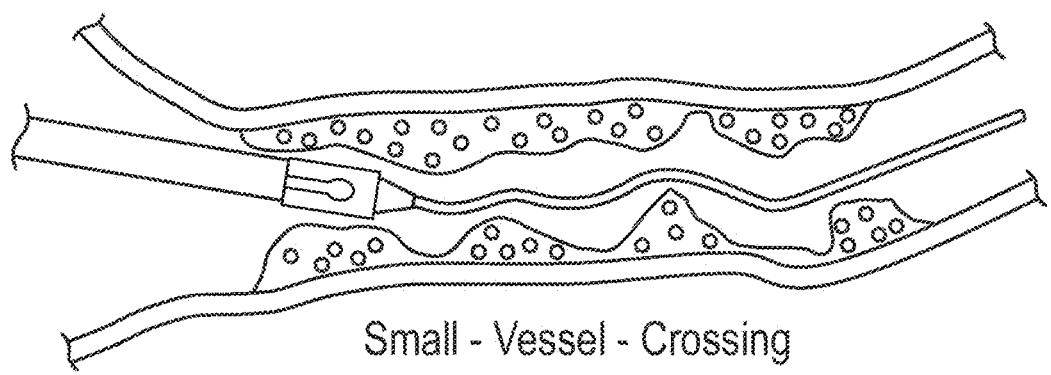
FIG. 2B illustrates an exemplary shock wave angioplasty catheter being in a blood vessel highly narrowed by a partial occlusion, according to one or more aspects of the present disclosure.

FIG. 2B depicts the catheter 10 being used in a small vessel that is highly narrowed by a partial lesion. In this situation, the guidewire can be advanced much farther into the lesion, and in some cases, all the way across the lesion (as shown in FIG. 2B). After positioning the guidewire, the catheter can be advanced through the lesion in incremental stages. At each stage, the flexible cap is pressurized, and shock waves are generated to break up the occlusion and increase the diameter of the blood vessel. Optionally, the flexible cap may remain pressurized while the catheter is advanced through the lesion. As noted above, once the diameter of the vessel is sufficiently large, a larger-diameter catheter may be advanced through the vessel to complete the treatment.

Figure 3A:
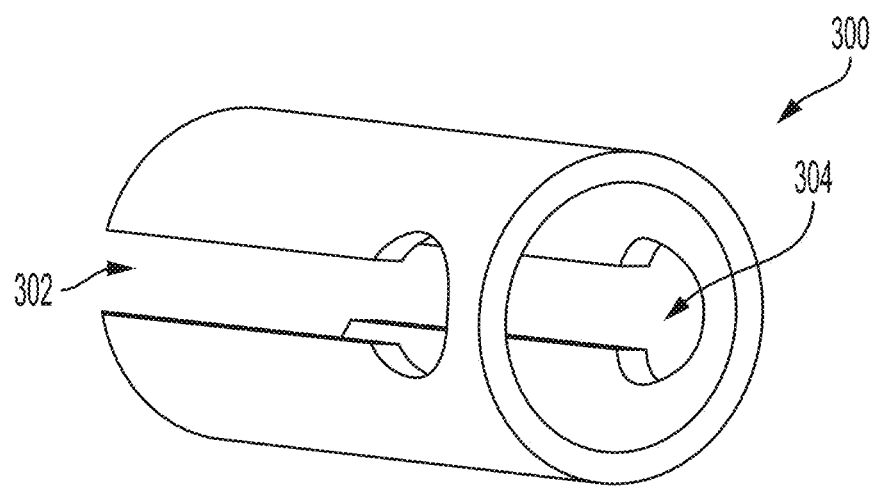
FIG. 3A illustrates a perspective view of an exemplary slotted emitter sheath of an emitter having slots with a circular end, according to aspects of the present disclosure.

FIG. 3A illustrates a perspective view of an exemplary slotted emitter sheath 300 of an emitter having slots with a circular end. The emitter sheath 300 can be incorporated into a shock wave generator such as the shock wave generator 16 of catheter 10 of FIG. 1 and may serve as an electrode of an electrode pair in an emitter. The emitter sheath 300 includes a pair of slots 302 extending along a length of the emitter sheath 300 that terminate with a circular cutout 304. The cut-out can be any variety of geometries, such as a triangular, square, rectangular, octagonal, hexagonal, elliptical, etc., and the circular shape used herein is provided for example only. Incorporating a shape with smoothed edges (e.g., circular, elliptical, etc.) rather than a shape with sharp edges may improve the structural integrity of the emitter sheath 300, because shapes with sharp edges may introduce residual stress peaks that tend to crack the sheath of the emitter sheath 300. The slots 302 and cutout 304 regions can enable placement of a wire or another electrode proximate to the distal end of the emitter sheath 300, which can encourage forward-biased shock waves.

Figure 3B:
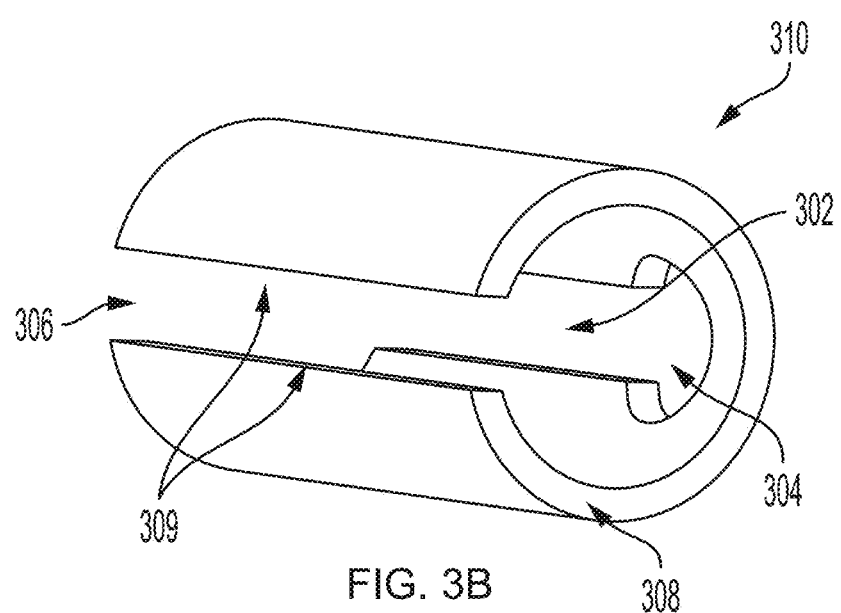
FIG. 3B illustrates a perspective view of an exemplary slotted emitter sheath of an emitter having a straight cutout, according to aspects of the present disclosure.

FIG. 3B illustrates another variation of a slotted emitter sheath 310 that can be incorporated in an emitter of a catheter. The emitter sheath 310 can be incorporated into a shock wave generator such as the shock wave generator 16 of catheter 10 of FIG. 1 and may serve as an electrode of an electrode pair in an emitter. The slotted emitter sheath 310 includes a first slot 302 that terminates with a circular cutout 304 and a second slot 306 that extends across the entire length of the emitter sheath 310. Again, the circular cutout 304 is exemplary and may be implemented with any number of shapes. The second slot 306 can enable placement of a wire or another electrode near the distal face 308 of the emitter sheath 310, which can encourage forward-biased shock waves.

Figure 3C:
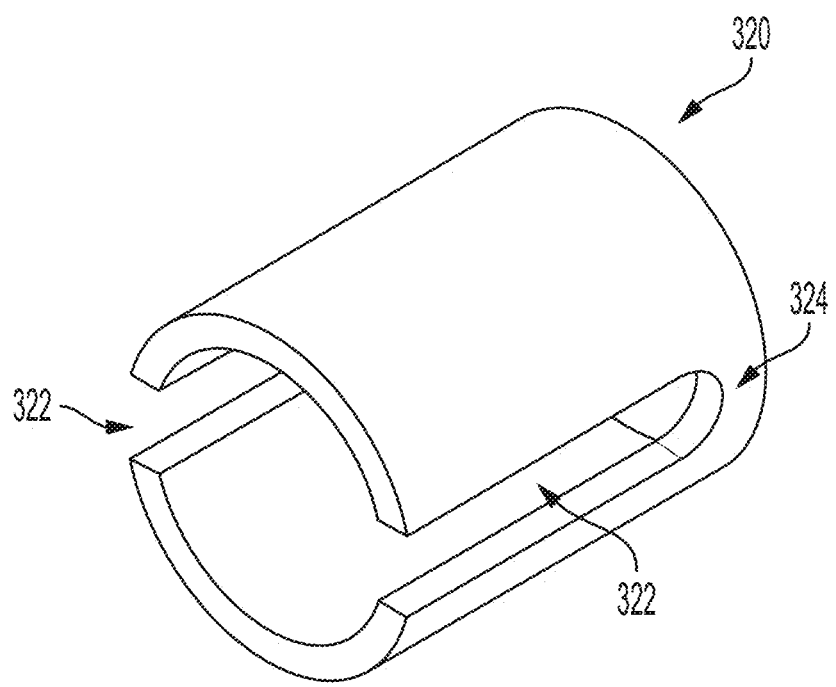
FIG. 3C illustrates a perspective view of an exemplary slotted emitter sheath of an emitter having slots with a rounded end, according to aspects of the present disclosure.

FIG. 3C illustrates another variation of a slotted emitter sheath 320 that can be incorporated in an emitter of a catheter. The emitter sheath 320 can be incorporated into a shock wave generator such as the shock wave generator 16 of catheter 10 of FIG. 1 and may serve as an electrode of an electrode pair in an emitter. The slotted emitter sheath 320 includes two slots 322 that terminate with a rounded cutout 324. Incorporating rounded cutouts 324 may promote forward-biased shock waves, in that the shock waves generated when a wire or another electrode is placed near the distal end of the slot 322 close to the distal end of the rounded cutout 324.

In variations in which the slotted emitter sheath serves as an electrode of an electrode pair in an emitter, the other electrode of the pair can include a wire that is positioned within the slot, as will be discussed further below. When voltage is supplied to a wire and across an electrode pair and shock waves are generated, however, the most distal portion of the wire can erode (e.g., retreat from the distal end of the wire towards the proximal end of the wire). As the wire erodes and the furthest distal portion recedes, the origin point from which shock waves are generated may also recede. Accordingly, it may be beneficial for the slot of an emitter to include at least a portion that extends circumferentially around the emitter sheath, rather than only along a longitudinal axis of the emitter sheath.

Figure 3D:
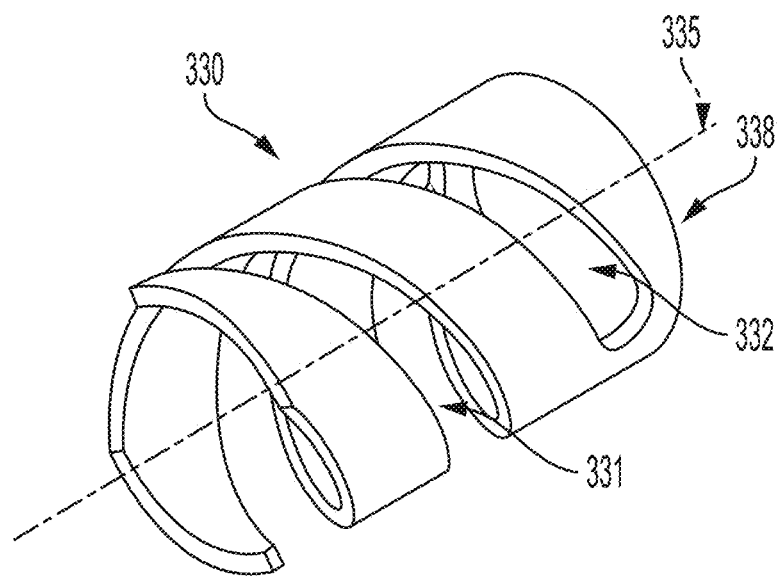
FIG. 3D illustrates a perspective view of an exemplary slotted emitter sheath of an emitter having helical slots, according to aspects of the present disclosure.

FIG. 3D illustrates another variation of a slotted emitter sheath 330 that can be incorporated in an emitter of a catheter. The emitter sheath 330 can be incorporated into a shock wave generator such as the shock wave generator 16 of catheter 10 of FIG. 1 and may serve as an electrode of an electrode pair in an emitter. The slotted emitter sheath 330 includes two helical slots 331 and 332, with at least a portion of these slots extending circumferentially around the emitter sheath relative to the longitudinal axis 335 of the emitter sheath. Wires that lay within the path of either helical slots 331 and 332 can be insulated albeit with exposed distal ends, which act as electrode surfaces forming electrode pairs with the material of emitter sheath 330. The helical shape of the helical slots 331 and 332 can ensure that even as a wire retreats in a proximal direction due to erosion from shock wave generation, the wire is following the path of helical slot 331 and/or 332, and the origin point of the shock waves (jumping from the distal end of the wire to the slotted emitter sheath 330) remains adjacent to the distal end 338 of the slotted emitter sheath 330 for a longer period. Accordingly, incorporating a helical slotted sheath can promote forward biased shock waves for a longer period than an emitter sheath having one or more slots that do not have a helical path.

Figure 3E:
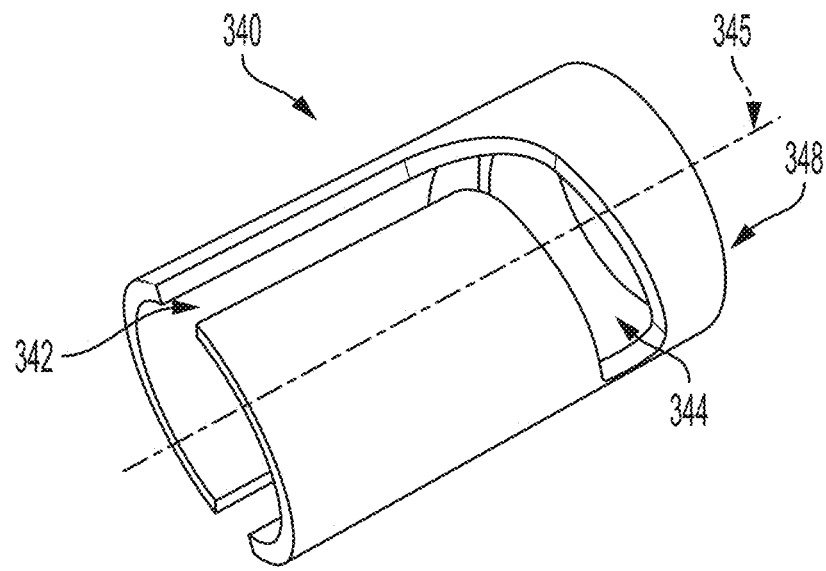
FIG. 3E illustrates a perspective view of an exemplary slotted emitter sheath of an emitter having contorted slots, according to aspects of the present disclosure.

Another design which similarly encourages forward biased shock waves for a longer period is shown in FIG. 3E, which illustrates another variation of a slotted emitter sheath 340 that can be incorporated in an emitter of a catheter. The emitter sheath 340 can be incorporated into a shock wave generator such as the shock wave generator 16 of catheter 10 of FIG. 1 and may serve as an electrode of an electrode pair in an emitter. The slotted emitter sheath 340 includes a pair of slots 342 that terminate with a contorted end 344 (colloquially referred to as a "hockey stick" path), which extends circumferentially around the emitter sheath relative to the longitudinal axis 345 of the emitter sheath. Wires that lay within the path of either slot 342 with contorted end 344 can be insulated albeit with exposed distal ends, which act as electrode surfaces forming electrode pairs with the material of emitter sheath 340. Similarly to the helical slots above, the contorted end 344 can promote forward biased shock waves for a longer period. For example, if a wire is placed within the slot 342 and then shock waves are generated, even as the wire retreats within the slot due to erosion from shock wave generation (e.g., retreating from the distal end of the wire towards the proximal end of the wire), the distal end of the wire nonetheless remains roughly parallel to the distal end 348 of the slotted emitter sheath 340 for a longer period than an emitter sheath having slots that do not include a contorted end.

The emitter sheath 300 is a generally cylindrical sheath. The emitter sheath 300 may be formed from a variety of lightweight conductive materials, including metals and alloys such as stainless steel, cobalt chromium, platinum chromium, cobalt chromium platinum palladium iridium, or platinum iridium, or a mixture of such materials. In one or more examples, a catheter may include a plurality of slotted emitters positioned at various locations along a length of the catheter (e.g., longitudinally spaced apart from one another), and may include a combination of slotted emitters with any variation of slots, such as the slots with circular cutouts as shown with respect to the slotted emitter sheath 300, through cut slots as shown with respect to the slotted emitter sheath 310, slots with rounded ends as shown with respect to the slotted emitter sheath 320, helical slots as shown with respect to the slotted emitter sheath 330, and/or contorted slots as shown with respect to the slotted emitter sheath 340.

Figure 4A:
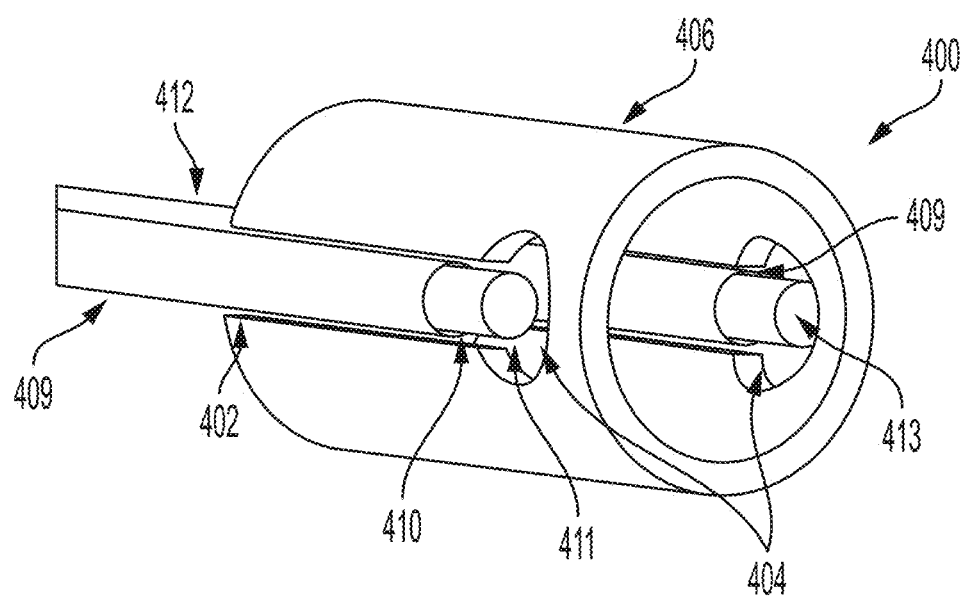
FIG. 4A illustrates an exemplary emitter, according to aspects of the present disclosure.

FIG. 4A illustrates an exemplary emitter 400, according to aspects of the present disclosure. The emitter 400 includes an emitter sheath 406, a lead wire 410, and a return wire 412. The emitter sheath 406 here contains a pair of slots 402 that each terminate with a circular cutout 404, like the emitter sheath 300 of FIG. 3A. The lead wire 410 is positioned in one of the slots 402 such that a distal face 411 of the lead wire 410 is located in the circular cutout 404. Similarly, the return wire 412 is positioned in the other slot 402 such that the distal face 413 of the return wire 412 is located in the circular cutout 404.

Each of the lead wire 410 and the return wire 412 can be insulated wires with insulation 409 extending along the length of the wire (e.g., from a proximal connection to a voltage source to a distal position as part of an electrode assembly). The wires may be cylindrical wires (as shown in FIG. 4A) or may be flat wires. Optionally, the wires may include a flattened or crimped portion, such as a crimped distal end. The wires may have a diameter that is the same as the thickness of the emitter sheath 406 such that the wires are coplanar with the outer surface of the emitter sheath 406. The wires may instead have a greater diameter than the emitter sheath 406 such that the wires extend farther outward than the emitter sheath 406. When the wires have a diameter that is greater than the thickness of the emitter sheath 406, the cavitation bubbles and/or shock waves generated by the emitter 400 may propagate generally outward in all directions from the distal end of each wire.

At least a portion of the lead wire 410 is exposed to form an electrode of an electrode pair opposite a section of electrode sheath 406 of the emitter 400. Similarly, at least a portion of the return wire 412 is exposed to form an electrode of an electrode pair opposite a section of electrode sheath 406 of the emitter 400. The exposed portion (e.g., the non-insulated or insulated removed portion) of each wire can be an area of the wire wherein the insulating layer that surrounds the insulated wire is exposed, or wherein a strip of the insulating layer is removed. The insulation-removed portion may include just the distal faces 411 and 413 of the lead wire 410 and return wire 412. Optionally, the non-insulated portion of the wires can include a larger portion of the wire than just the distal face or distal end. For instance, the distal tip, including a portion of the shaft of the wire and the distal face, may form the non-insulated portion of the wire (as depicted in FIG. 4A). As shown in FIG. 4A, both an insulated portion and a non-insulated exposed portion of the lead wire 410 and return wire 412 is positioned in the slot 402. Where the non-insulated portion of the wires is the distal end of the wire, a majority of the length of the slot comprises the insulated portion of the wire. Optionally, rather than including a distal end that is located in the slot, the return wire can be connected to a proximal end of the conductive sheath.

The emitter 400 includes two electrode pairs, a first pair including the distal face 411 of the lead wire 410 and a first circular cutout 404 of the emitter sheath 406 (more particularly, a surface of the circular cutout that is proximate to the distal face 411), and a second pair including the distal face 413 of the return wire 412 and a second circular cutout 404 of the emitter sheath 406. Where the emitter instead includes a slot that extends along the entire length of the emitter (e.g., slot 306 of FIG. 3B), a surface of the slot and/or of the distal end of the emitter sheath forms the electrode of the electrode pair. For example, referring to FIG. 3B, the portion of the emitter sheath 310 that forms an electrode can be the distal face 308 and/or one or both inner faces 309 of the slot 306.

The distal faces 411 and 413 of the lead wire 410 and return wire 412 are each separated from an inner surface of the circular cutout 404 of the emitter sheath 406 by a gap. When voltage is applied across the lead wire 410 and the return wire 412, current flows across the gaps to generate shock waves. For instance, current may flow from the distal face 411 of the lead wire 410 to the emitter sheath 406 by jumping across the gap between the distal face 411 and the inner face of the cutout 404 and then travel from the emitter sheath 406 to the return wire 412 by jumping across the gap between the inner face of the cutout 404 to the distal face 413 of the return wire 412.

The lead wire 410 receives voltage from a voltage source (such as voltage source 28 of FIG. 1) and delivers that voltage to the emitter sheath 406. The return wire 412 receives voltage from the emitter sheath 406 and returns that voltage to the voltage source (e.g., to complete the circuit). In one or more examples, the lead wire 410 (also called the "hot wire") may deliver greater voltage. Thus, the gap adjacent to the lead wire 410 can generate a larger shock wave that exhibits increased pressure than the shock wave generated adjacent to the return wire 412. The lead wire 410 may be located in a cutout 404 as shown in FIG. 4A, and/or may be located in a slot that extends along the entire length of the emitter sheath 406 (such as 306 of emitter sheath 310 of FIG. 3). Similarly, the return wire 412 may be located in a cutout such as cutout 404 and/or a slot that extends along the entire length of the emitter sheath 406. In one or more examples, the polarity of the lead wire 410 and the return wire 412 may be switched. In such case, the return wire 412 will act as the "lead" and deliver voltage to the emitter sheath 406 while the lead wire 410 will act as the "return" and return that voltage to the voltage source. Accordingly, the terminology of "lead" and "return" as it relates to the lead wire 410 and the return wire 412 is provided for example only, as both wires may serve as a "lead" or "return" depending on the polarity of the wires as they connect to a voltage source. Additionally, polarity may be switched during use such that a lead wire in one instance is the return wire in another instance.

By locating the lead wire 410 and return wire 412 in the slots 402 such that the insulation-removed portions (e.g., the distal faces 411 and 413) are located proximate to a distal end of the emitter sheath 406, the emitter 400 promotes forward-biased and/or distally directed shock waves that are generated when current jumps across the gaps between the electrodes of each respective electrode pair. That is, shock waves generated when current jumps, for example, from the distal face 411 of the lead wire 410 to the emitter sheath 406, will propagate in a forward direction (e.g., to the right based on the orientation shown in FIG. 4A). Encouraging shock waves to propagate in a forward direction, i.e., in a forward-biased configuration, can more efficiently break up occlusions that are proximate to a forward end of the catheter, and thus can be desirable when treating a tight occlusion, such as a CTO, because it enables the catheter to be incrementally advanced farther within the occlusion and/or to create a channel through the occlusion.

In addition to promoting forward-biased shock waves, locating the lead wire 410 and return wire 412 in the slots 402 of the emitter sheath 406 also reduces the overall diameter of the emitter 400 relative to a configuration wherein the wires are located within the emitter sheath 406 (e.g., in the interior of the emitter sheath 406). Reducing the overall diameter of the emitter 400 improves the navigability of the catheter within tight occlusions, as it enables the catheter to be advanced within smaller spaces than a catheter with a larger overall diameter.

Figure 4B:
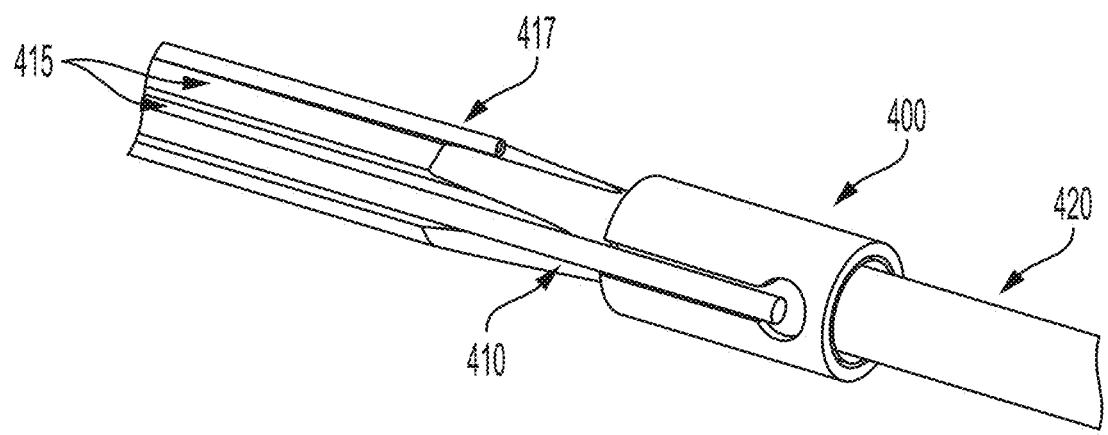
FIG. 4B illustrates a top perspective view of an exemplary emitter mounted to an elongate tube, according to aspects of the present disclosure.

Another design configuration that reduces the overall diameter of the catheter is incorporating grooves in the elongate tube that receive the wires of the emitter 400. FIG. 4B illustrates a top perspective view of the emitter 400 mounted to an elongate tube 420, as the emitter 400 may be mounted within a catheter. The elongate tube 420 includes one or more grooves 415 that extend along the length of the elongate tube. The lead wire 410 is positioned in one of the grooves 415. On the opposite side, the return wire can also be positioned in another groove (not visible in figure). By locating the wires (e.g., lead wire 410 and return wire 412) in grooves rather than on the outer surface of the elongate tube 420, the overall diameter of the emitter 400 when mounted to the elongate tube 420 is reduced. Accordingly, a catheter that incorporates the emitter 400 with the elongate tube 420 having grooves 415 exhibits improved navigability and crossing ability relative to a catheter with an elongate tube without grooves.

Figure 4C:
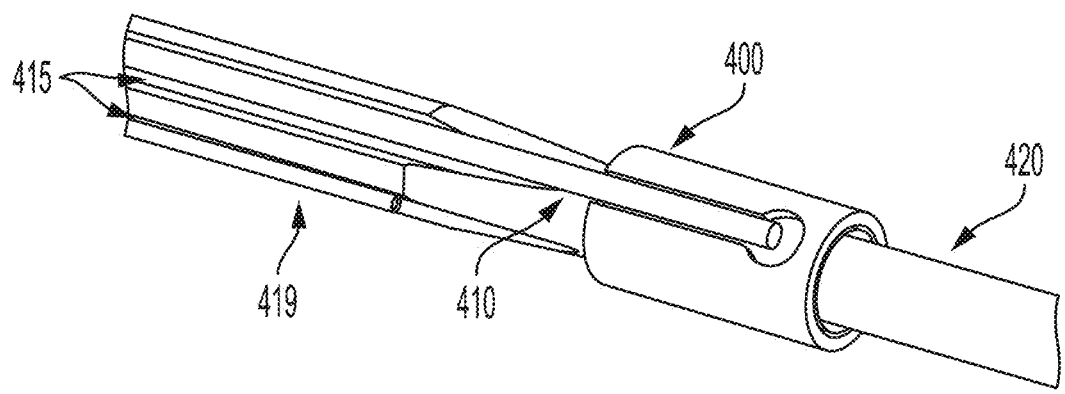
FIG. 4C illustrates a bottom perspective view of an exemplary emitter mounted to an elongate tube, according to aspects of the present disclosure.

As shown in FIG. 4B, an inlet lumen 417 is positioned in one of the grooves 415 of the elongate tube 420. An outlet lumen 419 is shown in FIG. 4C, which illustrates the bottom perspective view of the emitter 400 mounted to the elongate tube 420. The inlet lumen 417 and outlet lumen 419 can be used to evacuate air bubbles created proximate to the emitter 400 by shock waves forming and bursting. For instance, when the emitter 400 is surrounded by a fillable member (such as flexible cap 18 of FIG. 1), the inlet lumen 417 can supply a flow of fluid to the region within the fillable member that then flows out the outlet lumen 419, thereby evacuating the air bubbles created by shock waves forming and bursting. After evacuating air bubbles during a treatment period, the system can be "closed" by closing off the outlet lumen 419 (e.g., preventing fluid from flowing out the outlet lumen 419) and then applying pressure via the inlet lumen 417 to repressurize the fillable member before a subsequent treatment period. The inlet and outlet lumens can remove bubbles continuously, which can limit the amount that the fillable member expands during a treatment period. In one or more examples, rather than having a separate inlet lumen and outlet lumen, a single lumen can act as a combined flush lumen. In this context, the flush lumen can be a single lumen acting both as an inlet (pushing fluid into the saline chamber to flush out bubbles) and outlet (removal of bubbles out of chamber and out of device).

The placement and spacing of the electrode pairs can be controlled to provide a more effective shock wave treatment. For instance, the electrode pairs of a shock wave generator may be spaced circumferentially around the distal end of the catheter in consistent increments, e.g., 180 degrees apart or 90 degrees apart, to generate shock waves evenly around the catheter. The electrode pairs of the emitter 400 of FIG. 4A are circumferentially spaced apart from one another by 180 degrees (e.g., on opposite sides of the emitter sheath 406 from one another). In one or more examples, the electrode pairs may instead by circumferentially spaced apart from one another (which can be referred to as "offset") by less than 180 degrees, which may encourage the shock waves generated by the respective electrode pairs to constructively interfere with one another. Moreover, the emitter 400 may include more than two electrode pairs to encourage the generation of additional shock waves when voltage is supplied to the emitter sheath 406.

Figure 5A:
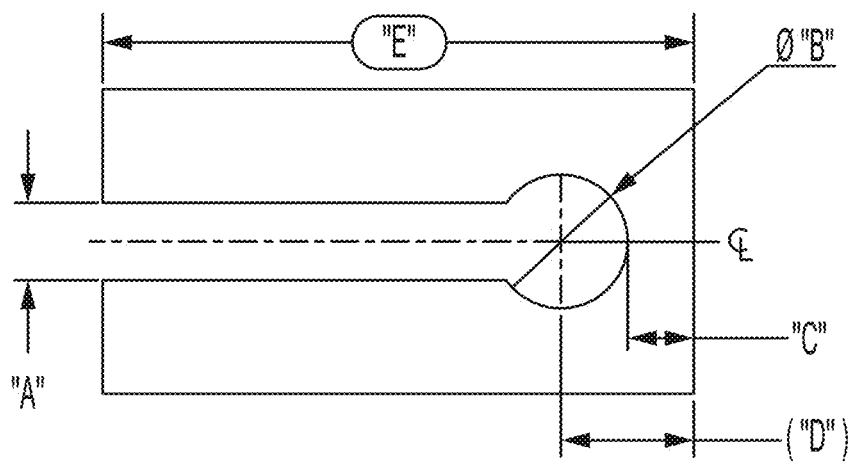
FIG. 5A illustrates an exemplary slotted emitter sheath, according to aspects of the present disclosure.

FIG. 5A illustrates a plan drawing showing a slotted emitter sheath. According to one or more examples, the dimension "A," which corresponds to the width of a slot (e.g., slot 402 of FIG. 4A), may be 0.008 inches. Dimension "B," which corresponds to the diameter of a circular cutout (e.g., cutout 404 of FIG. 4A), may be 0.014 inches. Dimension "C," which corresponds to a distance from the distal end of the emitter sheath to the most distal portion of the cutout, may be 0.005 inches. In one or more examples, dimension "C" may instead be 0.010 inches. Dimension "D," which corresponds to a distance from the distal end of the emitter sheath to a center point of the cutout may be 0.012 inches. Optionally, dimension "D" may be 0.017 inches. In one or more examples, dimension "D" may correspond to the most distal end of a wire when the wire is positioned in the slot. Dimension "E," which corresponds to the length of the slotted emitter sheath may be, for example between about 0.02-0.12 inches. In one or more examples, the length of the slotted emitter sheath may be more than 0.12 inches, such as 0.2 inches 0.3 inches, 0.4 inches, and increments and gradients of length therein. In one or more examples, the length of the slotted emitter sheath may be less than 0.02 inches, such as 0.01 inches.

Figure 5B:
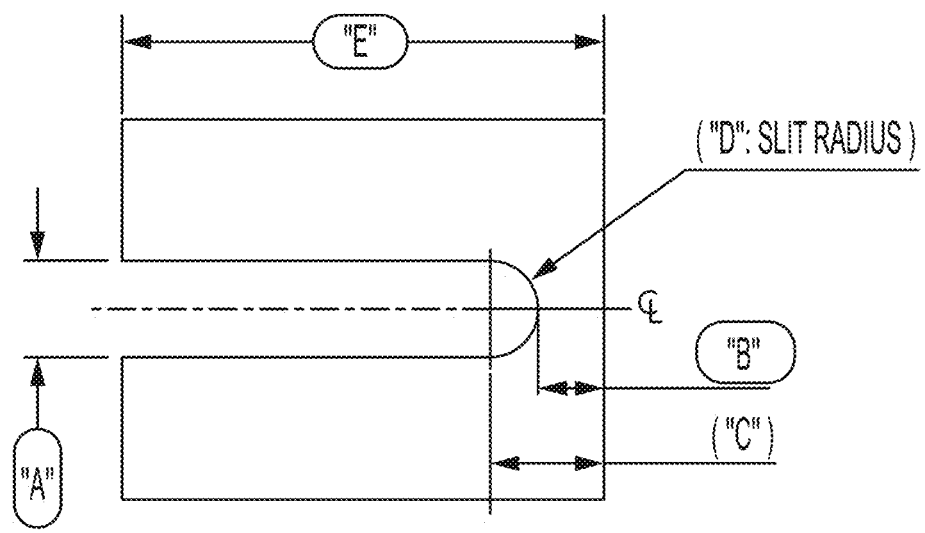
FIG. 5B illustrates an exemplary slotted emitter sheath, according to aspects of the present disclosure.

FIG. 5B illustrates a plan drawing showing a slotted emitter sheath. As compared to FIG. 5A, the slot of slotted emitter sheath depicted in FIG. 5B does not terminate with a circular cutout. Instead, the slot terminates with a curved distal end. In one or more examples, rather than a curved distal end, the slot may terminate with a straight distal end (e.g., a rectangular cutout). The dimensions of the slotted emitter sheath of FIG. 5B, namely the width of the slot (dimension "A"), the distance from the distal end of the emitter sheath to the most distal portion of the cutout (dimension "C"), and the distance from the distal end of the emitter sheath to a center point of the distal portion of the slot (dimension "D") may be the same as the measurements of the slot of FIG. 5A.

FIG. 6A illustrates the distal end of an exemplary catheter 602 with a shock wave generator including an emitter 603 that surrounds a number of lumens, and FIG. 6B illustrates the cross-sectional view of the catheter 602 cut across plane 6X. The catheter 602 has an emitter 603 having an emitter sheath 610 that surrounds a pair of insulated wires 613, a guidewire lumen 611 that receives a guidewire, an inlet lumen 616 and an outlet lumen 618. As visible in FIG. 6B, the emitter sheath 610 is the outermost component of the emitter 603 of catheter 620 and the emitter sheath 610 surrounds each of the interior lumens. The catheter 620 has an overall diameter dz. The overall diameter $d_1$ of the catheter 602 may be, for example, 1.4 mm or 1.5 mm, and increments and gradients of range therein.

FIG. 6C illustrates the distal end of an exemplary catheter 620 with a shock wave generator that has a slotted emitter 621, and FIG. 6D illustrates the cross-sectional view of the catheter 620 cut across plane 6Y. The catheter 620 includes a slotted emitter 621 having an emitter sheath 606 with a pair of slots 604 that receive wires 613. The catheter 620 can be configured as the catheter 10 of FIG. 1, and can include an electrode assembly such as the emitter 400 of FIGS. 4A and 4B, and/or an emitter with a slot that extends across the length of the emitter, such as the emitter sheath 310 with slot 306 of FIG. 3B. The catheter 620 has an overall diameter $d_2$. The overall diameter $d_2$ of the catheter 620 may be less than 1.5 mm. For instance, the overall diameter $d_2$ may be 1.3 mm, 1.35 mm, 1.40 mm, or 1.45 mm, and increments and gradients of range therein.

As compared to the catheter 602, the catheter 620 includes wires 613 located in grooves of the elongate tube (such as grooves 415 of elongate tube 420 FIG. 4B) and positioned in the slots 604 of the emitter sheath 606 (such as slots 402 of emitter sheath 406 of FIG. 4A). By locating the wires 613 of the catheter 620 in slots of an emitter sheath rather than within an emitter sheath and positioning the wires 613 within grooves along the elongate tube (as shown in FIG. 4B), the overall diameter $d_2$ of the catheter 620 is less than the diameter $d_1$ of the catheter 602. Accordingly, the catheter 620 achieves a smaller crossing profile, which improves the navigability of the catheter 620, especially within hard-to-cross occlusions. For example, a catheter with a small overall diameter can burrow farther into a tight occlusion or a CTO and to create a channel when crossing the occluded area of the vessel.

Additionally, by positioning the distal end of the wires 613 proximate to the distal end of the emitter sheath 606, the origin of the shock waves generated via the emitter 621 (from the current jumping between the wires and the emitter sheath) is proximate to the distal end of the emitter sheath 606. Placing the origin of the shock waves proximate to the distal end of the emitter sheath 606 enables the catheter 620 to generate shock waves that are forward-biased and with the most distal portion of those shock waves applying spherical pressure against occlusions that are in front of the catheter 620. In contrast, the origin of the shock waves generated by the catheter 602 is not as proximate to the distal end of the emitter. Accordingly, less (or none) of the spherical pressure of the shock waves generated by the catheter 602 does not impinge against the occlusions that are in front of the catheter 620 and instead dissipates as it propagates generally outwardly. Accordingly, as compared to the catheter 602, the catheter 620 generates forward-biased shock waves and harnesses the distal spherical pressure of these waves to break up occlusions in front of the catheter 620 thus enabling the catheter 620 to be advanced farther within tight occlusions.

In one or more examples, a catheter comprising a slotted emitter sheath, such as the catheter 620, can include of one or more coatings and/or liners that can reduce (or prevent) friction and/or drag when using the catheter. Friction and/or drag may be generated, for example, between the outer surface of a catheter and the vessel and/or between an internal guidewire lumen of the catheter and a guidewire as the catheter is inserted into a body lumen. To reduce friction and/or drag, a catheter can include a coating and/or liner at one or both of these interfaces. For example, the catheter can include a coating and/or liner on a portion or the entirety of an inner surface of a guidewire lumen that receives a guidewire. For instance, the catheter 620 can include a coating and/or liner on the inner surface of the guidewire lumen 611 to prevent or reduce friction and/or drag between the guidewire lumen 611 and a guidewire as the catheter 620 travels along a guidewire positioned in the guidewire lumen 611. In addition or alternatively, a catheter can include an external coating and/or a liner on the external surface of the catheter. For example, the catheter 620 could include a coating and/or liner on the outer surface of the catheter 620 to prevent or reduce friction and/or drag between the catheter 620 and the body lumen the catheter 620 is traveling through.

By incorporating one or more liners and/or coatings that reduce or prevent friction and/or drag, the catheter can travel more easily within the body lumen, which can improve the device tracking and enable the catheter to reach and treat more distal lesions than a catheter without liners and/or coatings. Materials that a liner and/or coating may include that can reduce friction and/or drag include, for example, polymeric materials such as polytetrafluoroethylene (PTFE) and high density polyethylene (HDPE), hydrophilic or hydrophobic coatings, etc.

Exemplary uses of IVL devices as described herein can follow a therapeutic procedure as follows. Identification of a target lesion (e.g., a CTO) within patient vasculature (e.g., coronary, peripheral, etc.) is done with real-time or prior-to-procedure imaging or sensing. An IVL catheter having a forward-biased shock wave generator is introduced into the patient vasculature and deployed at one end of the target lesion site. The IVL catheter is then operated to have electrical current delivered to the electrodes and across the spark gaps of the electrode pairs to thereby generate shock waves. Due to the structure of the emitter(s), the shock waves are biased in a relatively forward direction, toward and/or past the distal end of the catheter. The shock waves subsequently encounter and disrupt (break up, crack, etc.) the target lesion. The disruption of the target lesion can allow for advancement of the IVL catheter into or further within the target lesion, where additional cycles of shock wave generation can be executed, thereby further disrupting the target lesion. After the target lesion has been sufficiently disrupted following one or more cycles and or one or more advancements through the lesion, the IVL catheter can be withdrawn from the target region of the patient vasculature.

Although the electrode assemblies and catheter devices described herein have been discussed primarily in the context of treating coronary occlusions, such as lesions in vasculature, the electrode assemblies and catheters herein can be used for a variety of occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

The elements and features of the exemplary electrode assemblies and catheters discussed above may be rearranged, recombined, and modified, without departing from the present invention. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:
1. A catheter for treating an occlusion in a body lumen, the catheter comprising:
   an elongate tube;
   a member sealed to a distal end of the elongate tube that is fillable with a conductive fluid;
   a cylindrical conductive sheath circumferentially mounted around the elongate tube within the member, the conductive sheath comprising first and second slots extending along a length of the conductive sheath from a proximal end of the conductive sheath toward a distal end of the conductive sheath, wherein at least one of the first and second slots comprises a longitudinally extending portion that extends parallel to a longitudinal axis of the conductive sheath from the proximal end of the conductive sheath toward the distal end of the conductive sheath and a circumferentially extending portion that extends circumferentially around at least a portion of the conductive sheath with respect to the longitudinal axis; and
   first and second wires extending distally along the elongate tube into the first and second slots, wherein distal ends of the first and second wires are positioned proximally of a distal end of the conductive sheath and are spaced apart from the conductive sheath by respective gaps in an arrangement such that when a voltage pulse is supplied to the first and second wires current flows across the gaps to generate cavitation bubbles and/or shock waves.

2. The catheter of claim 1, wherein a majority of the at least a portion of at least one of the first and second wires that is in the slot is insulated.

3. The catheter of claim 1, wherein at least one of the first and second slots terminates with a cutout, and the distal end of a corresponding one of the first and second wires is positioned in the cutout.

4. The catheter of claim 3, wherein the cutout is spaced apart from the distal end of the conductive sheath.

5. The catheter of claim 3, wherein the cutout comprises a circular shape.

6. The catheter of claim 5, wherein the circular shape has a diameter that is greater than a width of the respective slot.

7. The catheter of claim 1, wherein the at least a portion of the at least one of the first and second slots comprises a helical shape.

8. The catheter of claim 1, wherein at least one of the first and second slots extends along the entire length of the conductive sheath.

9. The catheter of claim 1, wherein the elongate tube comprises at least one groove extending along a length of the elongate tube, and wherein the at least one of the first and second wires extends along the at least one groove of the elongate tube.

10. The catheter of claim 1, wherein each of the first and second wires comprises an insulating layer wrapping around a length of the wire, and wherein the distal end of each of the first and second wires is exposed from the insulating layer to form a non-insulated distal end.

11. The catheter of claim 1, wherein each of the first and second wires comprises an insulating layer wrapping around the insulated wire, and wherein a strip of the insulating layer is removed to form a non-insulated distal end.

12. The catheter of claim 1, wherein at least a portion of at least one of the first and second wires is flattened.

13. The catheter of claim 1, wherein the elongate tube comprises a guidewire lumen for receiving a guidewire, and wherein the catheter is configured to be advanced into the body lumen over the guidewire.

14. The catheter of claim 1, wherein the elongate tube comprises one or more flush lumens for removing the cavitation bubbles and/or shock waves from within the member.

15. The catheter of claim 1, wherein the circumferentially extending portion extends less than one turn around the longitudinal axis of the sheath.

16. A system for treating an occlusion in a body lumen comprising:
    a catheter comprising:
        an elongate tube;
        a member sealed to a distal end of the elongate tube that is fillable with a conductive fluid;
        a cylindrical conductive sheath circumferentially mounted around the elongate tube within the member, the conductive sheath comprising a first slot and a second slot extending along a length of the conductive sheath from a proximal end of the conductive sheath toward a distal end of the conductive sheath, wherein at least one of the first and second slots comprises a longitudinally extending portion that extends parallel to a longitudinal axis of the conductive sheath and a circumferentially extending portion that extends circumferentially around at least a portion of the conductive sheath with respect to the longitudinal axis;
        a first insulated wire extending distally along the elongate tube into the fist slot, the first insulated wire having an insulated portion and a non-insulated distal end, both the insulated portion and the non-insulated distal end being disposed in the first slot, wherein the non-insulated distal end is positioned proximally of the distal end of the conductive sheath and spaced apart from the conductive sheath by a gap;
        a second insulated wire extending distally along the elongate tube into the second slot, the second insulated wire having an insulated portion and a non-insulated distal end, both the insulated portion and the non-insulated distal end being disposed in the second slot, wherein the non-insulated distal end is positioned proximally of the distal end of the conductive sheath and spaced apart from the conductive sheath by a gap; and
        a power source that supplies the first insulated wire and the second insulated wire with a voltage pulse causing current to flow across the gap between the non-insulated distal end of the first insulated wire and the conductive sheath and the gap between the non-insulated distal end of the second insulated wire and the conductive sheath to generate cavitation bubbles and/or shock waves at each gap.

17. The system of claim 16, wherein a majority of a length of the first slot has the insulated portion of the first insulated wire positioned within and a majority of a length of the second slot has the insulated portion of the second insulated wire positioned within.

18. The system of claim 16, wherein the first slot terminates with a cutout that is spaced apart from the distal end of the conductive sheath, and the non-insulated distal end of the first insulated wire is positioned in the cutout and the second slot extends along the entire length of the conductive sheath.

19. The system of claim 16, wherein the first slot and the second slot each terminates with a cutout that is spaced apart from the distal end of the conductive sheath, and wherein the non-insulated distal end of the first insulated wire is positioned in the cutout of the first slot and the non-insulated distal end of the second insulated wire is positioned in the cutout of the second slot.

20. The system of claim 19, wherein the cutout of each of first slot and the second slot comprises a circular shape.

21. The system of claim 16, wherein the at least a portion of the at least one of the first and second slots comprises a helical shape.

* * * * *